(12) United States Patent
Neuta Arciniegas et al.

(10) Patent No.: US 11,696,973 B2
(45) Date of Patent: Jul. 11, 2023

(54) FLEXIBLE TISSUE REGENERATION IMPLANT

(71) Applicants: Universidad del Valle, Cali (CO); Universidad Autonoma de Occidente, Cali (CO)

(72) Inventors: Paola Andrea Neuta Arciniegas, Cali (CO); Alvaro Jose Rojas Arciniegas, Cali (CO); Jose Oscar Gutierrez Montes, Cali (CO)

(73) Assignees: UNIVERSIDAD DEL VALLE, Cali (CO); UNIVERSIDAD AUTONOMA DE OCCIDENTE, Cali (CO)

( * ) Notice: Subject to any disclaimer, the term of this patent is extended or adjusted under 35 U.S.C. 154(b) by 0 days.

(21) Appl. No.: 15/973,512

(22) Filed: May 7, 2018

(65) Prior Publication Data

US 2019/0321518 A1    Oct. 24, 2019

(30) Foreign Application Priority Data

Apr. 24, 2018    (CO) .................. NC2018/0004340

(51) Int. Cl.
*A61L 27/38*    (2006.01)
*A61L 27/24*    (2006.01)

(52) U.S. Cl.
CPC ........... *A61L 27/3886* (2013.01); *A61L 27/24* (2013.01); *A61L 2300/64* (2013.01); *A61L 2430/20* (2013.01)

(58) Field of Classification Search
None
See application file for complete search history.

(56) References Cited

U.S. PATENT DOCUMENTS

| | | | |
|---|---|---|---|
| 5,891,558 A * | 4/1999 | Bell .................... | A61L 27/3633 428/218 |
| 2014/0050766 A1 * | 2/2014 | Levenberg ............ | A61L 27/225 424/400 |
| 2014/0099709 A1 * | 4/2014 | Presnell .............. | A61L 27/3834 435/347 |

OTHER PUBLICATIONS

Murphy et al. "Evaluation of hydrogels for bio-printing applications." Journal of Biomedical Materials Research Part A 101.1 (2013): 272-284. (Year: 2013).*

* cited by examiner

*Primary Examiner* — Emily A Cordas
(74) *Attorney, Agent, or Firm* — The Morales Law Firm; Joseph L. Morales

(57) ABSTRACT

This invention discloses an implant for regeneration of tissue with lesions, comprising a mixture with different types of cells, particularly, mesenchymal stem cells (MSC), endothelial cells, and specific functional cells according to the nature and function of the tissue, included into the biocompatible polymeric matrix, where the cells may or may not be organized in a specific way. This innovation also discloses a method to manufacture the implant. The implant of the present invention is useful for replacement or regeneration of animal and human tissues.

8 Claims, 6 Drawing Sheets

FLEXIBLE TISSUE REGENERATION IMPLANT

CROSS-REFERENCE TO RELATED APPLICATIONS

This application claims priority under 35 U.S.C 119(a) from Colombian patent application number NC2018/0004340, filed on Apr. 24, 2018, which is incorporated herein by reference in its entirety.

FIELD OF THE INVENTION

The present invention is related to the field of tissue engineering and regenerative medicine, and especially to the techniques of regeneration of animal and human tissues. Particularly, this innovation refers to an implant for tissue regeneration and a method to manufacture the implant.

BACKGROUND OF THE INVENTION

The tissues are composed of a combination of cells with extracellular matrix, having specific characteristics that provide the required functionality according to their location. Some tissues are composed of cells with high reproduction rates, being the cells permanently renewed, while other tissues have very low and even no cellular regeneration rates.

The therapeutic alternative for regeneration of these tissues ranges from the use of cell proliferation-stimulating drug products to the transplantation of whole organs, depending on the severity of the damage and the ability to self-regeneration.

The aging of the world population, the incidence of diseases demanding tissue replacement, the low availability of organs for transplantation, the complications of rejections due to incompatibility, and the progress of therapeutic techniques, among others, have led to the development of scientific research focused on tissue engineering for solving these problems.

Tissue engineering makes use of a combination of biomaterials with specialized cells and advanced manufacturing techniques, offering a product that can be integrated into the organ to be regenerated, allowing repair by means of cell therapy.

Among the limiting factors of cell therapy is the survival of the implant, because cells must be implanted, integrated into the tissue, and survive for a period of time not yet defined in order to benefit the tissue that receives the cell therapy.

In the particular case of heart disease, the main complication is heart failure, which is a complex clinical syndrome that can result from any structural or functional damage to the heart, impairing the ability of the ventricle to fill and/or eject blood. The main features of heart failure are dyspnea and fatigue that limit exercise tolerance, and fluid retention that leads to pulmonary congestion and peripheral edema (Zipes D P, Libby P, Bonow R O, Braunwald E. Braunwald's Heart Disease: a text book of cardiovascular medicine. 7th edition. Elsevier Saunders 2005. p. 539).

In those cases, the heart cannot regenerate the lost tissue and replace it with functional tissue. Cardiomyocytes (cardiac muscle cells capable of contracting spontaneously and individually) are divided during the fetal stage and suffer hypertrophy after birth, accompanied by changes in the proteomic profile which prevent them from reproducing throughout human maturity (Bicknell K A, Coxon C H, Brooks G. Can the cardiomyocyte cell cycle be reprogrammed? J Mol Cell Cardiol 2007; 42:706-72. This lack of cell multiplication means that, in the face of myocardial damage, cardiac remodeling occurs (a phenomenon which is a repairing process by means of mobilization of peripheral circulation or bone marrow stem cells to the site of the lesion (Qian H, Yang Y, Huang J, Dou K, Yang G. Cellular cardiomyoplasty by catheter-based infusion of stem cells in clinical settings. Transplant Immunology 2006; 16:135-147).

After myocardial infarction occurs, the body's repair process begins to try to restore normal cardiac function. The degree of recovery depends on the type of injury, going from non-recovery to almost complete recovery. After myocardial infarction, the heart usually recovers rapidly during the first days and weeks, reaching almost full recovery in weeks 5 to 7, although the process may continue for months [6] (Guyton A, Hall J. Tratado de fisiologia médica. 9a edición. Philadelphia, Pa., U.S.A, W.B. Saunders Co, 1996. P. 289).

In the medical literature, multiple therapeutic strategies have been reported to decrease the impact of heart failure on the quality of life of the patient, including long-term pharmacological treatments, implantable devices (artificial heart, counterpulsation pumps, etc.), surgical techniques for the transposition of striated muscle, partial or total cardiac autotransplantation and xenotransplantation, and new techniques of treatment with cells of different origins to restore the contractile function of the myocardium.

Currently, therapeutic efforts are focused in two directions: on one hand, the design and manufacture of small, autonomous and biocompatible biomedical devices that can replace the heart pump; and on the other hand, the treatment with injected cells able to integrate into the tissue at the site of the lesion.

Notwithstanding multiple studies carried out with different cell types in the treatment with injected cells able to integrate into the tissue at the site of the lesion, conclusive results have not yet been obtained. For example, in relation to state of the art patented inventions similar to the present one, the patent ES2334298 discloses a construct formed by a biologically compatible biomaterial, which serves as a support, on which one or more types of living cells are grown; the cells being selected from osteoblasts, fibroblasts, condroblasts and mesenchymal cells, thus obtaining a complex three-dimensional structure. The supportive biomaterial used to prepare the construct of the invention described in S2334298 is either mesostructured silica (SBA-15) and/or a biomaterial made of a silica matrix of the SBA-15 type, on which nanoparticles of calcium hydroxyapatite (HA) grow.

U.S. Pat. No. 7,214,371 discloses a method that provides a three-dimensional porous polysaccharide matrix, on which mammalian cells are grown in vitro; the cells are selected from the group of fetal cardiac cells, neonate cardiac cells, fibroblasts, smooth muscle cells, endothelial cells, skeletal muscle miocytes, mesenchymal stem cells and embryonic stem cells to form a biograft. The scar tissue or dead tissue is optionally removed from the implantation site before transplantation of the biograft. The polysaccharide matrix further comprises controlled release polymer microspheres, being capable of releasing soluble angiogenic growth factors in a controlled way.

The patent application US2008/0226726 describes a pharmaceutical composition comprising a gel-based biodegradable matrix, at least one active ingredient, and stem cells capable of differentiating into cardiac tissue, in the form of a patch for the treatment of heart failure due to myocardial infarction.

However, the previously exposed solutions in some cases either use non-biological matrixes, or are invasive when removing the living tissue together with the dead tissue, or use only stem cells in the matrix. Under the referred conditions, the present invention solves the problems related to transplantation procedures involving the repair or regeneration of tissues, by means of an implant comprising a combination of mesenchymal stem cells, endothelial cells, and functional cells specific to the tissue to be regenerated.

BRIEF DESCRIPTION OF THE INVENTION

One exemplary tissue regeneration implant, comprises a biocompatible polymeric matrix; a combination of mesenchymal stem cells (MSC); endothelial cells, and functional cells specific to the tissue. The mesenchymial stem cells (MSC), the endothelial cells and the functional cells specific to the tissue are embedded in the biocompatible polymeric matrix.

In one embodiment, the number of mesenchymal cells (MSC) present in the implant range between 10% and 80% of total cells in the implant. In turn, the number of endothelial cells range between 10% and 80% of total cells in the implant, and the number of functional cells specific to the tissue range between 10% and 80% of total cells in the implant.

In a further embodiment, mesenchymal stem cells (MSC), endothelial cells and functional cells specific to the tissue are in a ration of 1:1:1, respectively.

In another exemplary embodiment, the number of total cells in the biocompatible polymeric matrix is between $3 \times 10^5$ and $9 \times 10^5$ per $mm^3$. One embodiment comprises mesenchymal stem cells (MSC) obtained from the bone marrow (of the patient or a suitable donor); endothelial cells selected from the group consisting of: differentiated mesenchymal stem cells (MSC) into vascular endothelium and cells obtained from a vascular endothelial tissue, as well as combinations of those cells; and the specific functional cells are selected from the group consisting of: mesenchymal stem cells (MSC) differentiated into the specific cellular type of the tissue and cells obtained from the tissue, as well as combinations of those cells.

In another embodiment, the biocompatible polymeric matrix is type 1 collagen. Preferably, mesenchymal stem cells (MSC); endothelial cells; and functional cells specific to the tissue are either uniformly embedded in the polymeric matrix, or also, the cells may be embedded in a non-uniform way in the polymeric matrix.

A second object of the present invention is a method to manufacture a tissue regeneration implant, comprising the following stages:
scattering mesenchymal stem cells (MSC), endothelial cells and functional cells specific to the tissue;
adding a precursor of the biocompatible polymeric matrix; and
allowing the polymerization of the precursor to form a biocompatible polymeric matrix embedded with th mesenchymal stem cells (MSC), endothelial cells and functional cells specific to the tissue.

The previously described embodiments, as well as any additional embodiments, as applicable, are further described below

DETAILED DESCRIPTION OF THE INVENTION

Figure 1:
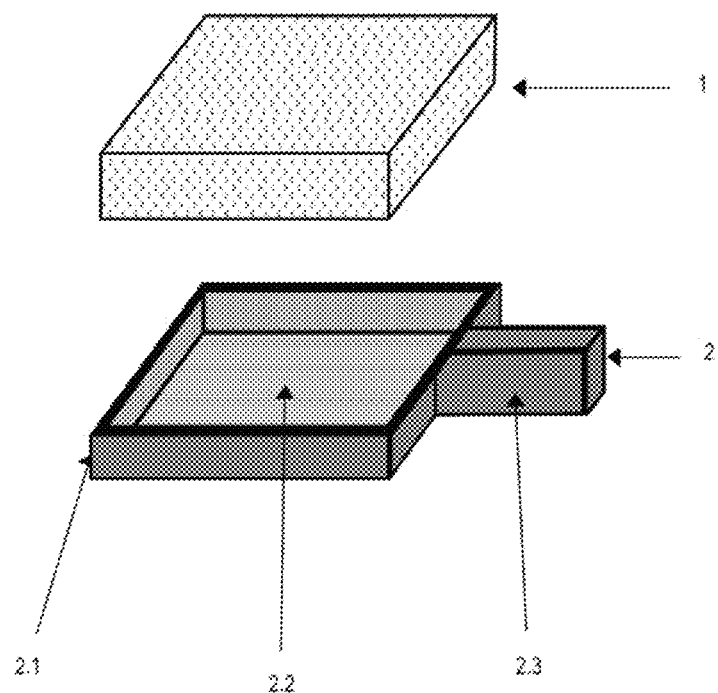
FIG. 1 shows the structure of the implant (1) and the base (2) for manufacturing the implant.
Figure 2:
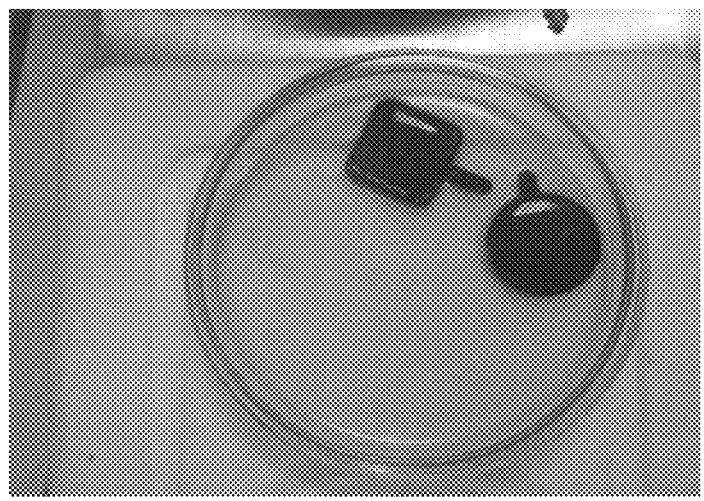
FIG. 2 shows a photograph of the implant with different types of geometry.
Figure 3:
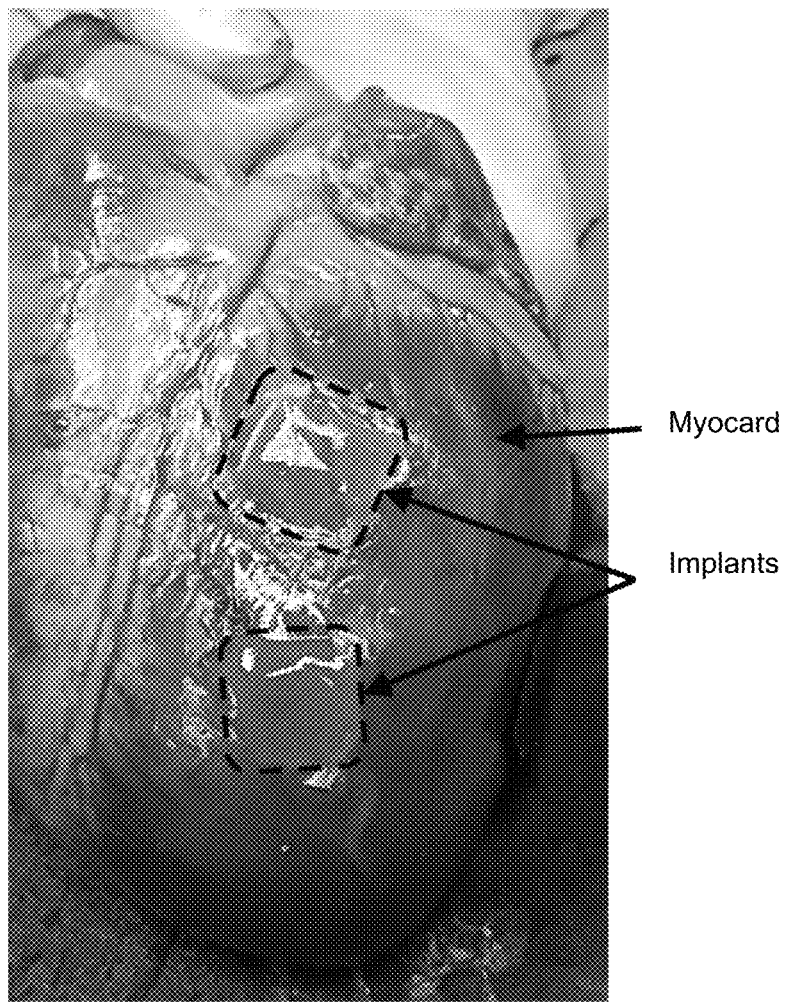
FIG. 3 shows a photograph of one of the embodiments of the implant fixed in the heart of a pig biomodel ex-vivo.

The description of this invention is not intended to limit its scope, but to serve as a particular example of such description. A knowledgeable individual in the subject is expected to understand that the equivalent embodiments do not deviate from the real spirit and the scope of the present innovation in its broadest form.

For a better comprehension of the present application, certain technical terms used in its description will be detailed below.

Within the context of this application "mesenchymal stem mothers" or "MSC" are multipotent or pluripotent cells originated in the mesodermal germinal layer having the capacity to differentiate into different cellular types.

Within the context of this application "endothelial cells" or "vascular endothelial" cells are the cells forming a unicellular layer covering the internal surface of the blood vessels and forming the wall of the veins, arteries and capillaries.

Within the context of this application "biocompatible polymeric matrix" is matter formed by n units of monomers that join together to create long chains of such monomers, and are compatible for using in mammals, particularly in humans, without rejections or adverse effects.

This application discloses a novel implant for regeneration of flexible tissues that comprises a biocompatible polymeric matrix formed by polymerization of components of the extracellular matrix, seeded with the appropriate cell types, which are mesenchymal stem cells, endothelial cells, and specific functional cells according to the nature and function of the tissue to be regenerated, cells which may or may not be organized in a specific way in the matrix. These MSC cells play the role of immunomodulation in the acute immunologic response environment at the site of the injury; they are also the source of cells that can be potentially differentiated into the cellular type required by the tissue in its repair process. On the other hand, the cells differentiated into vascular endothelium (endothelial cells) are cells used as input for angiogenesis, and differentiated cells are capable of regenerating the specific tissue at the site of the injury. Together, they offer a unique and efficient implant for the regeneration of injuries in different mammal tissues.

In one embodiment, the number of mesenchymal stem cells (MSC) range between 10% and 18% of total cells in the implant. In turn, the number of endothelial cells range between 10% and 18% of total cells in the implant, and the number of functional cells specific to the tissue range between 10% and 80% of total cells in the implant. In another embodiment, the number of mesenchymal stem cells (MSC) present in the implant range between 20% and 50% of total cells in the implant, the number of endothelial cells range between 20% and 50% of total cells in the implant, and the number of functional cells specific to the tissue range between 20% and 50% of total cells in the implant.

In some embodiments, mesenchymal stem cells (MSC), endothelial cells and functional cells specific to the tissue are in a ratio of 1:1:1, respectively.

In another embodiment, the number of total cells in the biocompatible polymeric matrix is a sufficient amount of cells to trigger a regenerating effect in a particular tissue, which can be adjusted depending on the volume of the implant to be generated and which is intimately related to the size of the injury to be repaired. Preferably, the number of total cells is between $3 \times 10^5$ and $9 \times 10^5$ per $mm^3$ of the polymeric matrix.

In another embodiment, mesenchymal cells are obtained from bone marrow, while endothelial cells are selected from a group comprised of: mesenchymal stem cells differentiated into vascular endothelial cells and cells obtained from a vascular endothelial tissue, as well as combinations of those cells, and the specific functional cells are selected from the group comprised of: mesenchymal stem cells (MSC) differentiated into the specific cellular type of the tissue and cells obtained from the tissue, as well as combinations of the cells.

In another embodiment, the biocompatible polymeric matrix is polymerized type 1 collagen, a protein that is part of the extracellular matrix of animal tissues and which thanks to its mechanic resistance, is able to support, for example, heart contractile movements without deformation, while offering a support that allow cells to remain at the implantation site for the ultimate integration with the surrounding healthy tissue. However, the present invention is not limited to the use of this particular polymeric matrix, but any biocompatible polymeric matrix can be used according to the state of the art technology. In a preferred embodiment, the biocompatible polymeric matrix is a re-absorbable type of matrix, forming pores during polymerization allowing cells to arrange and move within those spaces, and serving as support to these cells by establishing links with the cellular anchoring proteins of the surrounding tissue.

In one exemplary embodiment, mesenchymal stem cells (MSC); the endothelial cells; and the functional cells specific to the tissue to be regenerated are uniformly embedded in the biocompatible polymeric matrix. In another modality, these cells are embedded in the biocompatible polymeric matrix in a non-uniform way. In other words, the cells may or may not be embedded uniformly. Uniformity of embedding of the cells, or the lack thereof, does not affect the effectiveness of the implant in regenerating damaged tissue. For example, cells may occupy the entire matrix, however, either they could be clustered per type of cell, or two types of cells may be in a localized area of the implant and the other may be uniformly distributed throughout the matrix. In other embodiment, the cells may be localized in a specific portion of the matrix, or there may be areas of the matrix with or without cells.

In one exemplary embodiment, in the case of transplantation procedures involving the regeneration of cardiac tissues, the implant consists of a biocompatible polymeric matrix that includes mesenchymal stem cells (MSC), cells differentiated into vascular endothelium and induced stem cells into cardiomyocytes. These cells may or may not be organized in a specific way in the matrix. Particularly, induced stem cells into cardiomyocytes are cells potentially able to integrate into the healthy myocardium around the infarcted site and contribute to the heart contractile function.

A second object of this invention is a method for manufacturing a tissue regeneration implant comprising the following stages:
scattering mesenchymal stem cells (MSC), endothelial cells and functional cells specific to the tissue;
adding a precursor of the biocompatible polymeric matrix; and
allowing the polymerization of the precursor to form a biocompatible polymeric matrix embedded with th mesenchymal stem cells (MSC), endothelial cells and functional cells specific to the tissue.

In a preferred embodiment, the number of mesenchymal stem cells (MSC) provided for manufacturing the implant range between 10% and 80% of total cells in the implant, more preferably between 20% and 50%, the number of endothelial cells provided range between 10% and 80% of total cells in the implant, more preferably between 20% and 50%, and the number of functional cells specific to the tissue provided range between 10% and 80% of total cells in the implant, more preferably between 20% and 50%.

Preferably, mesenchymal stem cells (MSC), endothelial cells and functional cells specific to the tissue provided to manufacture the implant are in a 1:1:1 proportion, respectively.

In another preferred modality, the number of total cells in the biocompatible polymeric matrix provided to manufacture the implant is between $3 \times 10^5$ and $9 \times 10^5$ per $mm^3$.

In a preferred modality, mesenchymal cells are obtained from bone marrow, while endothelial cells are selected from a group comprised of: mesenchymal stem cells differentiated into vascular endothelial cells and cells obtained from a vascular endothelial tissue, as well as combinations of those cells, and the specific functional cells are selected from the group composed of: mesenchymal stem cells (MSC) differentiated into the cellular type specific of the tissue and cells obtained from the tissue, as well as combinations of the cells.

Prior to polymerization, the precursor of the polymeric matrix is mixed into the mesenchymal stem cells, cells differentiated into vascular endothelium cells and specific functional cells. These cells may or may not be organized in a specific manner in the matrix.

In a preferred modality, the biocompatible polymeric matrix provided is type 1 collagen. This matrix is obtained by chemically polymerizing the biomaterial in presence of ammonium hydroxide vapor, for the required final consistency. The collagen matrix is an agonist in the functions of the organ that receives the implant and is useful to maintain the cells in the place of the implant until they are integrated into the surrounding tissue, while facilitating this integration due to the components used.

Preferably, mesenchymal stem cells; endothelial cells; and functional cells specific to the tissue are uniformly included into the polymeric matrix, or either the cells may scatter in a non-uniform way in the polymeric matrix. To achieve the desired endothelial cell arrangement, a three-dimensional printing process is performed by micro extrusion with two suspensions: one of the biocompatible polymeric matrix with the mesenchymal stem cells (MSCs) and the specific functional cells according to the nature and function of the tissue to be regenerated, and another one of the biocompatible polymeric matrix with endothelial cells.

In a preferred embodiment of this method, the polymeric matrix with the cells included inside is placed over a base having a particular shape and size, where the shape of the base is selected from geometrical shapes selected from the group consisting of as square, rectangular, circular, rhombus, rhomboid, trapezium, trapezoid and triangle, or has a shape dependent of the injury of the tissue to be regenerated. In turn, preferably, the particular size of the base depends on the size of the injury of the tissue to be regenerated. FIG. 1 shows an example of the implant (1) comprising the biocompatible polymeric matrix deposited on the base structure (2) providing support during the polymerization and implant processes, without affecting the composition and characteristics of the implant.

The biocompatible polymeric matrix may be manufactured from any biocompatible material. Some examples include polyester terephthalate glycol reinforced with 20% carbon fibers (PETG+CF0), polyvinyl chloride (PVC), polyoxymethylene (POM, also known as actal, polyacetal, or polyformaldehyde), polyether ether ketone (PEEK), polyamides (such as PA1010, PA11, PA12), styrene methyl methacrylate (SMMA), and other similar biocompatible polymeric matrices.

The implant is manufactured by the controlled placement of the precursor of the biocompatible polymeric matrix that contains mesenchymal stem cells (MSC), endothelial cells, and functional cells specific to the tissue in the base. This placement can be done by manual or automatic dosing of the suspension. Once the mixture of the precursor of the polymeric matrix and the cells is placed, it polymerizes to obtain the desired consistency and maintain the shape of the implant determined by the base.

The mentioned base (2) is made from a second polymer reinforced with natural or synthetic fibers, that allows the polymerization process of the implant biocompatible polymeric matrix and shape the implant (1). This base also facilitates the transport and manipulation processes of the implant for the implantation procedure.

The base (2) has the following characteristics: it is biocompatible to prevent any damage to the cells of the implant (1); it is sufficiently rigid and non-porous to contain the biocompatible polymeric matrix and give shape to the implant during the polymerization process; it is thin and flexible to allow its handling and adjustment to the conditions of the implant process; and it is non-adherent, so it can be detached from the implant in the implant process after the implant has been fixed to the tissue to be regenerated.

The base (2) has three sections: a lower plate (2.2), a surrounding wall (2.1), and a holding handle (2.3) that stands out to facilitate handling with surgical instruments at the time of implantation. The geometry and dimensions of the implant depend on the extent of the lesion of the tissue to be regenerated. In some embodiments, the polymeric matrix and cells are in a base with a particular form and shape. In some embodiments, the particular base is selected from geometrical shapes selected from the group consisting of as square, rectangular, circular, rhombus, rhomboid, trapezium, trapezoid and triangle. In some embodiments that base may have an irregular shape defined by the location in which it is to be used. In one such example, the shape of the particular base is dependent on the injury of the tissue to be regenerated. In other embodiments, the particular size of the base is dependent on the size of the injury of the tissue to be regenerated.

The examples below are intended to describe the most remarkable aspects of the invention, however they do not limit the scope of this invention.

EXAMPLES

Example 1. Obtaining and Characterizing MSC Cells

Figures 4A, 4B:
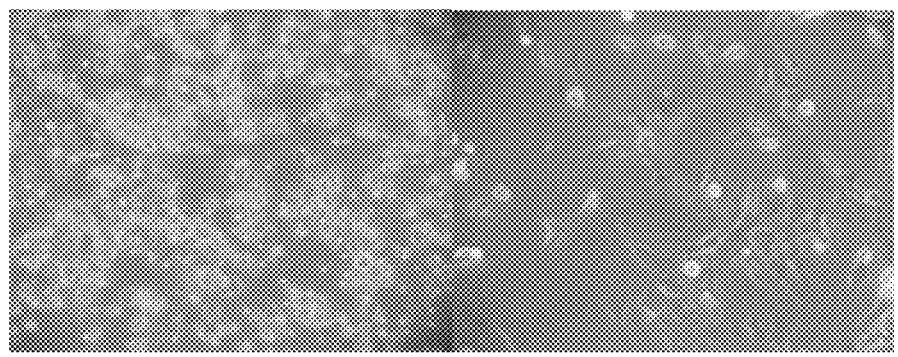
FIG. 4A shows a photograph of the microscopic view of the culture of MSC cells at 24 hours.
FIG. 4B shows photograph view of the microscopic view of the culture of MSC cells at 48 hours.

Mesenchymal stem cells (MSCs) were obtained from the bone marrow of the long bones (femurs and tibias) of male Wistar rats. Each bone was taken and both epiphyses were cut. The bone was washed with a syringe before extracting the bone marrow, collecting the material in a test tube. The marrow was washed with 1×HBSS, subjected to centrifugation at room temperature, placed in vials with culture medium for mesenchymal stem cells (MSCGM-CD™ Bullet Kit, Lonza), and placed in the incubator. At 48 hours, the vials were removed from the incubator and observed under an inverted microscope to verify the adhesion of the mesenchymal stem cells (FIG. 4).

The cells were maintained in culture, changing it to fresh medium until reaching a confluence of 90%.

The mesenchymal stem cells were characterized by immunocytochemistry (Cat. No. SCR018, Millipore). An aliquot of the initial vial was grown in an 8-well plate with 1×DMEM supplemented with 10% SFB, until reaching a confluence of approximately 90% in each well. Once this confluence was reached, the medium was removed by aspiration and the cells were fixed, covering them with 4% paraformaldehyde for 10 minutes.

The fixative was removed by aspiration and the wells were washed with 1×PBS (phosphate buffered saline). Each well was covered with blocking solution and left in incubation. Then, the blocking solution was aspirated and 100 µL of the primary antibodies were added to each well. The antibodies that were used were rabbit anti-integrin 131 (1/500), rabbit anti-type I collagen (1/500), rabbit anti-fibronectin (1/1,000), mouse anti-CD54 (1/100), mouse anti-CD14 (1/100), and mouse anti-CD45 (1/100). As fluorescence controls, 100 µL of mouse IgG (1 mg/mL) mixed with rabbit IgG (1 mg/mL) diluted in PBS 1× were added in a well, and 100 µL of diluted mouse IgG (1 mg/mL) in PBS 1× were added in another well.

Cells were incubated overnight with the primary antibodies. Cells were washed with 1×PBS the next day. As secondary antibodies, 100 µL of donkey anti-rabbit IgG, Cy3 conjugate (AP182C, Millipore) and anti-mouse IgG, Cy3 conjugate (AP192C, Millipore) diluted in a relation of 1:500 with 1×PBS were used, which were added in each well, as appropriate. Secondary antibodies were incubated at room temperature in the dark.

After the incubation time, wells were washed with 1×PBS. One hundred (100) µL of DAPI (4',6-diamidino-2-phenylindole dihydrochloride) were added to each well.

Under a confocal microscope, fluorescence was observed in the wells with anti-integrin β1, anti-type I collagen, anti-fibronectin, and anti-CD54. No fluorescence was observed in the wells with anti-CD14 and anti-CD45, neither in the negative controls. These characteristics coincide with those reported in the literature as typical of MSC cells.

At the moment of being required for injection to the biomodel, the mesenchymal stem cells (MSCs) were marked with 4',6-diamidino-2-phenylindole dihydrochloride (DAPI) (PA-3013, Lonza) to be traced in the histological analysis. To mark those cells, the culture flasks were washed with 1×HBSS, and 5 mL of 2.5% trypsin were added, incubating at 37° C. with 5% $CO_2$ until the cells were detached. Cells were collected in 50 mL tubes, washed with 1×HBSS and centrifuged at 2,500 revolutions per minute (r.p.m.) at room temperature. The cell count was made in a neubauer chamber and the number of cells was adjusted to a concentration of $1×10^5$ cells/mL with 1×DMEM. DAPI, a marker that adheres to the cell nucleus, was added at a 50 nM concentration, and cells were incubated at room temperature in the dark for 30 minutes. Cells were washed three times with 1×HBSS (Hank's balanced salt solution) and centrifuged at 2,500 r.p.m.

Example 2. Obtaining and Characterizing Cardiomyocytes Derived from Induced Stem Cells To obtain cardiomyocytes derived from induced stem cells to be used in the treatment, MSCs were thawed and the content of a complete vial was poured into a T-75 flask, adding 15 mL of conditioning medium made up of 1×DMEM, 20% SFB, 100 µM ascorbic acid (CC-4398, Lonza), 5 mg/mL of leukemia inhibitory factor (LIF3005, Chemicon), and 20 nM dexametasone (D-4902, Sigma-Aldrich), and incubating it at 37° C. with 5% $CO_2$.

Figure 5:
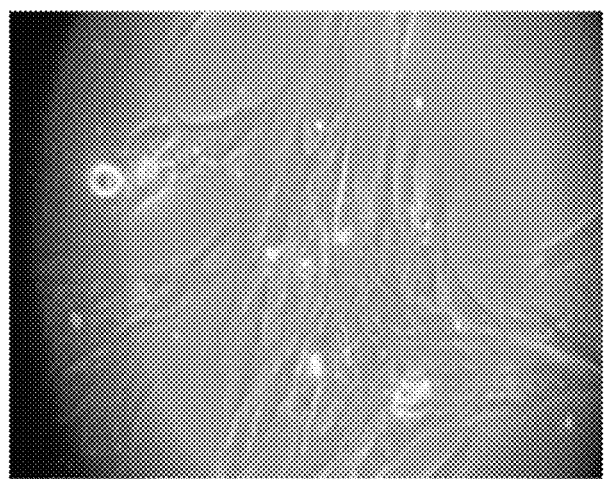
FIG. 5 shows a photograph of cardiomyocytes induced cells 15 days after the induction started.

Cells were grown to 60-70% confluence, and the culture medium was replaced by 1×DMEM, 2% SFB, 100 µM ascorbic acid, 20 nM dexamethasone, fibroblast growth factor (FGF) at 50 ng/mL (Cat. No. 13256029, Gibco), growth factor similar to insulin 1 (IGF-1) at 2 ng/mL (SRP4121, Sigma-Aldrich), and bone morphogenic protein 2 (BMP-2) at 10 ng/mL (PHC7145, Invitrogen. FIG. 5).

Cardiomyocytes derived from induced stem cells were characterized by immunocytochemistry (SCR059, Chemicon international). An aliquot of cells was placed in 8-well plates and allowed to dry on the plate in a humidity chamber at 4° C. Once the plate was dried, the cells were fixed with 4% paraformaldehyde in 1×PBS for 20 minutes at room temperature. The fixative was removed by aspiration and the cells were washed with 1×PBS. One hundred (100) µl of blocking solution was added to each well, which was made up of 5% SFB and 0.3% triton in 1×PBS, then incubated for two hours at room temperature, and finally the solution was aspirated and the primary antibodies were added.

One hundred (100) µL of the corresponding primary antibodies were added to the wells: sheep anti-tropomyosin (1/500), mouse anti-troponin I (1/100), mouse anti-actin (1/200), rabbit anti-ANP (1/200), and mouse anti-desmin (1/100). The negative staining controls were made by adding 100 µL of mouse, rabbit and sheep IgG, each one in each remaining well, diluted to 1 mg/mL in 1×PBS, and allowing the incubation. The wells were washed with 1×PBS and then with blocking solution. Then, 100 µL of the blocking solution was added to each well and left at room temperature.

The secondary antibodies used were: anti-mouse IgG, Cy3 conjugate, anti-rabbit IgG, Cy3 conjugate, anti-sheep IgG (AP184C, Millipore). These antibodies were added in the corresponding well, placing 100 µL of each one in a dilution of 1:500, after having aspirated the blocking solution.

The cells were incubated at room temperature. At the end of the incubation, the wells were washed with 1×PBS. One hundred (100) µL of DAPI were added to each well and incubated for 5 minutes, after which the excess was removed by washing it once with 1×PBS. Sheets were observed under a confocal microscope at 460 nm.

When observed under a confocal microscope, fluorescence was observed in the wells with anti-tropomyosin, anti-troponin 1, anti-actin, and anti-desmin antibodies. No fluorescence was observed in the wells with anti-ANP antibodies and in the negative controls.

When required for injection, the cardiomyocytes were washed with 1×HBSS, taken from the culture flask with 5 mL of 2.5% trypsin and incubated at 37° C. with 5% $CO_2$. They were collected in 50 mL tubes, washed with 1×HBSS and centrifuged at 2,500 r.p.m for 5 minutes at room temperature. The cell count was made in a neubauer chamber, the cells were re-suspended at a concentration of $1\times10^6$ cells/mL in 1×HBSS, and DiI (1,1'-Dioctadecyl-3,3,3',3'-tetramethylindocarbocyanine perchlorate) was added at a final concentration of 5 µM, adhering to the lipid bi-layers of the cells (Cat. No. 468495, Aldrich). Cells were incubated in the dark at 37° C. with 5% $CO_2$ for 20 minutes, and then washed three times with 1×HBSS.

Example 3. Obtaining and Characterizing Endothelial Cells

Figure 6:
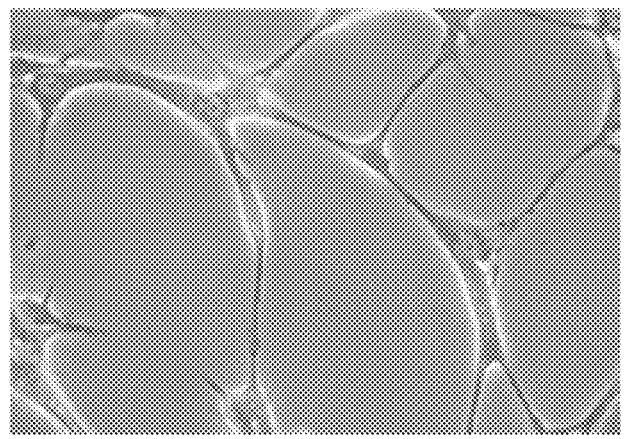
FIG. 6 shows a photograph of endothelial cells 21 days after the differentiation started.

The endothelial cells were obtained by differentiation from the MSCs. The vials with MSCs were thawed by immersion in a serological bath at 37° C. and the content of each vial was poured into a T-75 culture flask. Fifteen (15) mL of DMEM with 20% FBS were added and incubated at 37° C. with 5% $CO_2$ until reaching a confluence of 60-70%. Once this confluence was reached, the medium was replaced by 1×DMEM, supplemented with 5% FBS, vascular endothelial growth factor (VEGF) (PCH9394 Invitrogen) at 10 ng/mL, and fibroblast growth factor (FGF) (F0291 Sigma-Aldrich) at 2 ng/mL. Cells were maintained in the differentiation medium for several days (FIG. 6).

When the cells were required to be injected, the medium was discarded, the cells were washed with 1×HBSS, 5 mL of 2.5% trypsin was added, and the solution was incubated at 37° C. with 5% $CO_2$ until cells were detached. The cells were collected in 50 mL tubes, washed with 1×HBSS, and centrifuged at 2,500 r.p.m. at room temperature. The cell count was made in a neubauer chamber, the cell number was adjusted to a concentration of $1\times10^6$ cells/mL with 1×HBSS, DiO (3,3'-Dioctadecyloxacarbocyanine perchlorate) (D4292, Sigma) was added combined with cellular lipids at a concentration of 5 µM, and the solution was incubated at 37° C. with 5% $CO_2$ in the dark. At the end of the incubation, the cells were washed with 1×HBSS by centrifugation for 5 minutes at room temperature.

Example 4. Regeneration of the Infarcted Myocardium

Myocardial infarction was induced to chosen experimental biomodels, Wistar female rats (*Rattus norvegicus*), weighing between 250 and 300 grams, that were induced an acute myocardial infarction followed by reperfusion, by ligation of the descending left coronary artery.

The biomodels were divided into several groups described below:

Experimental Groups
a. Four groups of six rats each. At 15 days post-infarction, they were injected: (1) MSC, (2) cardiomyocyte induced cells, (3) cardiomyocyte induced cells with differentiated endothelial cells, (4) MSC with cardiomyocyte induced cells with differentiated endothelial cells.
b. Five groups of six rats each. At 15 days post-infarction, they were injected with the correspondent treatment directly in the heart with an insulin syringe, in four points of the borderline of the damaged zone and one in the center of the infarcted area: (1) MaxGel®; (2) type I collagen; (3) MaxGel® and type I collagen; (4) MaxGel®, MSCs, cardiomyocytes, and differentiated endothelial cells; (5) type I collagen, MSCs, cardiomyocytes, and differentiated endothelial cells. In other preferred embodiments, collagen base can be manufactured in a 3D printer including the cells. The 3D printed collagen and cell device can then be implanted in the appropriate location. The five components were mixed and injected directly in to the heart of the rats.
c. Two groups of six rats each. At 24 hours post-infarction, they were injected: (1) type I collagen, MSCs, cardiomyocytes, and differentiated endothelial cells; (2) type I collagen I, cardiomyocytes, and differentiated endothelial cells.

Control Groups d. A group of six infarcted rats that received no treatment.
e. A group of six rats that were injected the vehicle (PSS/Physiological Saline Solution) at 24 hours post-infarction.
f. A group of six rats that were injected the vehicle (PSS) at 15 days post-infarction.

The induction of acute myocardial infarction in the biomodels at the level of the left ventricle was made following the protocol published in 2004 by Tarnayski et. al. (Tarnayski O, McMullen J R, Schinke M, Nie Q, Kong S, Izumo S. Mouse cardiac surgery: comprehensive techniques for the generation of mouse models of human diseases and their application for genomic studies. Physiol. Genomics 2004; 16:349-360), which was adjusted to the rat model that was used. The left descending coronary artery was ligated into a secondary branch, causing a reduction in cardiac function, quantified as the reduction in the ejection fraction in relation to the initial value for each biomodel, measured by echocardiography.

On day 28 post-infarction, the biomodels were slaughtered by the injection of an intraperitoneal overdose (1 mL) of sodium pentobarbital. Immediately after the injection, the left side of the chest of the animal was opened, the afferent and efferent vessels of the heart were ligated and cut below the ligature, and the organ was completely removed from the cavity.

Once removed, the heart was washed with 4% paraformaldehyde in 1×PBS and perfused with the same solution, infusing it directly through the left coronary artery. A cross section of approximately 5 mm thick was made, leaving the infarcted area surrounded by healthy tissue, and the sample was immersed in 4% paraformaldehyde in 1×PBS for 24 hours. The following day, the tissue was transferred to 30% glucose in 4% paraformaldehyde in 1×PBS, and 24 hours later it was transferred to 1×PBS to complete the fixation. The tissue was cut with a cryostat to preserve the cell integrity and the labeling was done with dyes to each cell type, from the epicardium to the endocardium, in sections of 25 µm to 500 µm deep, obtaining three (3) plates for each biomodel.

The histological plates obtained were observed under the confocal microscope (LSM 700, Carl Zeiss) at 586 nm for emission and 554 nm for excitation to see the cells labeled with DiI (468495, Aldrich); at 450 nm for emission and 350 for excitation to see the cells labeled with DAPI (PA-3013, Lonza); and at 527 nm for emission and 514 nm for excitation for the cells labeled with DiO (D4292, Sigma).

After the analysis of the plates with a confocal microscope, two of the plates were stained with hematoxylin eosin (H-E) to analyze the local immunological reaction, and the third was stained with Masson's trichrome to observe the collagen in the tissue. These plates were observed with light microscopy.

Results

The study included only animals whose ejection fraction had fallen by at least 10% in relation to the initial measurement (p=<0.05).

TABLE No. 1

Fraction of final ejection (pre infarct) and post infarct (pre treatment) of biomodels of each group ($p < 0.05$).

| Group | Fe (media ± DS) | |
|---|---|---|
| | Pre infarct | Post infarct |
| MSC | 75,790 ± 2.17 | 51,140 ± 3.24 |
| Cardiomyocyte induced cells | 70,439 ± 2.42 | 60,411 ± 3.62 |
| Cardiomyocyte induced cells + endothelial cells | 69,722 ± 1.97 | 55,767 ± 2.96 |
| Cardiomyocyte induced cells + endothelial cells + MSC | 68,796 ± 1.97 | 52,579 ± 2.96 |
| Infarct with no treatment | 71,111 ± 1.97 | 61,204 ± 2.96 |
| Injection of SSF 15 d | 74,400 ± 2.16 | 56,111 ± 3.24 |

SD: standard deviation.

The biomodels allocated to the control group that was subjected to infarction and did not receive any treatment, showed a decrease of 15.4% in the mean of their ejection fractions, proving that in spite of the discontinuation of the stimulus (occlusion of the left descending coronary artery), the myocardium continued to lose functionality until the moment of slaughter (p=0.004). In the case of biomodels that received PSS (physiological saline solution) as treatment, the decrease in the ejection fractions after the injection was 8.5% (p=0.022). The statistical significance of these results shows that there is a marked loss of heart function after the infarction until the day of the slaughter of the biomodels.

The biomodels injected with MSCs alone had a decrease in the mean of the ejection fractions of 2.4%, when comparing the values before and after treatment (p=0.068); therefore, the injection of this type of cells alone did not stop the fall in cardiac function, which continued to decrease until the day of the slaughter of the animals, although not as significantly as in the control groups.

The biomodels that received cardiomyocytes had a decrease of 3.5%, when comparing the mean of the ejection fractions before and after treatment (p=0.136). In the group that received cardiomyocytes combined with endothelial cells, the difference between the means of the ejection fractions before and after treatment showed a 7.8% increase in cardiac function (p=0.160), while the difference in the biomodels that received the combination of the three types of cells showed a function recovery of 7.5% (p=0.098).

Given the little difference in improvement of cardiac function, measured by the ejection fractions, in the groups that received these last two treatments (p=0.0037) and considering the reported success with the use of MSCs, it was decided to use the combination of the three cell types with collagen and MaxGel matrices as the treatment to be tested. The comparison of the means of ejection fractions of the experimental groups that received some of the cellular treatments with the control groups, using single factor ANOVA, showed that the cellular injection prevented a continued fall of the ejection fraction, and even raised it with respect to the values post-infarction in some cases, as opposed to the control groups, where the cardiac function continued to decrease until the moment of slaughter of the biomodels (p=0.0002).

The biomodels of the control group that was subjected to infarction and did not receive treatment, showed a 15.4% decrease in the mean of the ejection fractions (p=0.004), while in the biomodels that received PSS as treatment, the decrease in the ejection fractions after the injection was 8.5% (p=0.022).

The biomodels injected with the MaxGel® matrix had a decrease in the mean of the ejection fractions of 14.7% when comparing the values before and after treatment (p=0.003). This statistical significance shows that the MaxGel® matrix did not stop the progressive fall of the ejection fraction of the biomodels. The group of biomodels that received MaxGel® seeded with the set complex consisting of cardiomyocytes, endothelial cells, and MSCs, had a decrease of 3.3% when comparing the mean of the ejection fractions before and after treatment. When this result is compared to the result obtained with the injection of the matrix alone, the conclusion is that it was the cells, not the matrix, that prevented a dramatic fall in cardiac function (p=0.013). The group that received collagen combined with MaxGel® showed an increase of 5.5% in the mean of ejection fractions, after treatment when comparing the values after being subjected to infarction (p=0.312).

For the biomodels that received collagen as treatment, the difference between the ejection fractions before and after treatment showed a recovery of 8.2%, indicating that collagen not only was able to prevent the progressive reduction of cardiac function, but to increase the cardiac function, as shown by the comparison to the condition of the animals after suffering the infarction (p=0.117). When implanting the collagen seeded with the group of cells consisting of cardiomyocytes, endothelial cells, and MSCs, the ejection fraction of the biomodels increased by 10.6% with respect to the values measured before treatment (p=0.014), which shows that this treatment would be the treatment of choice to try to prevent chronic heart failure after suffering a heart attack.

The biomodels of the group that underwent infarction without treatment showed a decrease of 15.4% in the mean of the ejection fractions (p=0.004), while the biomodels that received PSS as treatment 24 hours after the induction of infarction showed a drop in the ejection fractions of 12.7% (p=0.05).

The group of animals that received collagen seeded with cardiomyocytes, endothelial cells, and MSCs showed a recovery of 15.6% in the ejection fraction (p=0.023), while those injected with collagen seeded only with cardiomyocytes and endothelial cells showed an increase of 11.7% in the ejection fraction (p=0.031), meaning that the treatment of collagen with the complete group of cells improved the ejection fraction by 3.9% more than the group that received collagen seeded only with cardiomyocytes and endothelial cells (p=0.0000), according to the analysis by Anova.

TABLE No. 2

Fraction of ejection post-treatment biomodels.

| Group | FE (media ± DS) |
| --- | --- |
| MSC | 48,670 ± 2.93 |
| Cardiomyocyte induced cells | 56,915 ± 3.28 |
| Cardiomyocyte induced cells + endothelial cells | 63,611 ± 2.68 |
| Cardiomyocyte induced cells + endothelial cells + MSC | 60,079 ± 2.68 |
| Infarct with no treatment | 45,556 ± 2.68 |
| Injection of SSF 15 d | 47,667 ± 2.93 |

SD: standard deviation.

The analysis of the plates under a confocal microscope allowed to verify the presence of the marked cells up to 28 days after being implanted (slaughter day). The markers used to verify the survival of the implant do not seem to have spread to the neighboring cells, since the images were clear and the points of fluorescence well defined and limited. This proves the usefulness of DAPI (MSCs), DiI (cardiomyocytes) and DiO (endothelial cells) in the traceability of cellular implants in vivo.

The observation of the stained plates with H&E showed the characteristic healing of the infarcted myocardium in the chronic phase: at 43 days after the ischemic event in the animals that received treatment at 15 days, and at 29 days in those animals that were injected 24 hours after the infarction, the samples had a low granulocyte pattern and lot of space in which the pattern of striation of the muscle was lost and replaced by scar tissue. The presence of collagen fibers in the scar was evidenced by observing the stained layers with the Masson's trichrome technique.

In conclusion, the application of collagen only prevented the progressive decrease in cardiac function measured by the ejection fraction, but when it was used concomitantly with the group of cells (cardiomyocytes, endothelial cells and MSCs), it reestablished the contractile capacity of the myocardium to a good extent, proving that cellular regenerative medicine can contribute more than what is achieved solely by the thickening of the ventricular wall.

So it is feasible to conclude that the implant of the present invention is capable of producing the regeneration of flexible tissues by means of the implant formed by mesenchyme stem cells (MSCs), endothelial cells and specific functional cells according to the nature and function of the tissue to be regenerated, suspended in the biocompatible polymeric matrix. Therefore, it is useful in any transplant procedure that involves the regeneration of tissues.

Even though the present invention has been described with the preferred embodiments shown, it is understood that modifications and variations which fall within the spirit of this invention are within the scope of the following claims.

The invention claimed is:

1. A method for manufacturing a tissue regeneration implant, consisting of:
   scattering mesenchymal stem cells, endothelial cells selected from mesenchymal stem cells differentiated into vascular endothelial cells and cells obtained from a vascular endothelial tissue; and functional cells, wherein the functional cells are cardiomyocytes and wherein said cardiomyocytes are selected from mesenchymal stem cells differentiated into cardiomyocytes and cardiomyocytes obtained from a cardiac tissue;
   adding a precursor of a biocompatible re-absorbable polymeric matrix; and
   polymerizing the precursor to form a re-absorbable biocompatible polymeric matrix embedded with the mesenchymal stem cells, endothelial cells and functional cells, wherein the polymerization reaction is carried out in the presence of ammonium hydroxide vapor; and the re-absorbable biocompatible polymeric matrix comprises type 1 collagen.

2. The method of claim 1, wherein the mesenchymal stem cells (MSC) number ranges between 10% and 80% of total cells in the implant.

3. The method of claim 1, wherein the endothelial cells number ranges between 10% and 80% of total cells in the implant.

4. The method of claim 1, wherein the functional cells number ranges between 10% and 80% of total cells in the implant.

5. The method of claim 1, wherein the mesenchymal stem cells (MSC), endothelial cells, and functional cells are in 1:1:1 proportion respectively.

6. The method of claim 1, wherein the number of total cells in the biocompatible polymeric matrix is between $3 \times 10^5$ and $9 \times 10^5$ per $mm^3$.

7. The method of claim 1, wherein the mesenchymal stem cells (MSC) are obtained from bone marrow.

8. The method of claim 1, wherein the mesenchymal stem cells, endothelial cells and functional cells are viable up to 28 days after the polymerization reaction is carried out.

\* \* \* \* \*